United States Patent
Matsuzaki et al.

(10) Patent No.: US 7,053,206 B2
(45) Date of Patent: May 30, 2006

(54) METHODS AND COMPOSITIONS FOR MULTIPLEX AMPLIFICATION OF NUCLEIC ACIDS

(75) Inventors: Hajime Matsuzaki, Palo Alto, CA (US); Eric Murphy, San Francisco, CA (US)

(73) Assignee: Affymetrix, Inc., Santa Clara, CA (US)

( * ) Notice: Subject to any disclaimer, the term of this patent is extended or adjusted under 35 U.S.C. 154(b) by 77 days.

(21) Appl. No.: 10/743,376

(22) Filed: Dec. 23, 2003

(65) Prior Publication Data

US 2004/0126806 A1    Jul. 1, 2004

Related U.S. Application Data

(60) Division of application No. 09/989,441, filed on Nov. 21, 2001, now Pat. No. 6,673,579, which is a continuation of application No. 09/099,301, filed on Jun. 18, 1998, now Pat. No. 6,333,179.

(60) Provisional application No. 60/050,405, filed on Jun. 20, 1997.

(51) Int. Cl.
| C07H 21/04 | (2006.01) |
| C07H 21/02 | (2006.01) |
| C07H 21/00 | (2006.01) |
| C12Q 1/68 | (2006.01) |
| C12P 19/34 | (2006.01) |

(52) U.S. Cl. ............... 536/24.33; 536/23.1; 536/24.3; 536/25.3; 435/6; 435/91.1; 435/91.2

(58) Field of Classification Search ............ 435/6, 435/91.1, 91.2, 183; 436/94; 536/23.1, 536/24.3, 24.33, 25.3
See application file for complete search history.

(56) References Cited

U.S. PATENT DOCUMENTS

| 5,314,809 A | 5/1994 | Erlich et al. |
| 5,552,283 A * | 9/1996 | Diamandis et al. ............ 435/6 |
| 5,700,637 A | 12/1997 | Southern |
| 5,705,365 A | 1/1998 | Ryder et al. |

FOREIGN PATENT DOCUMENTS

| EP | 0 648 845 | 4/1995 |
| WO | WO 89/10977 | 11/1989 |
| WO | WO 96/01909 | 1/1996 |
| WO | WO 96/10648 | 4/1996 |
| WO | WO 96/39535 | 12/1996 |
| WO | WO 96/41012 | 12/1996 |

OTHER PUBLICATIONS

Haff, PCR Methods and Applications, vol. 3, pp. 332-337 (1994).

* cited by examiner

*Primary Examiner*—Frank Lu
(74) *Attorney, Agent, or Firm*—Banner & Witcoff, Ltd.

(57) ABSTRACT

A method is described for predetermining ratios of primer pairs present in a single reaction vessel so as to achieve approximately equimolar yield of products. The ratios are determined as a function of the length of the amplicon and the length of other amplicons being simultaneously tested. The primers may desirably be for p53 gene sequences.

18 Claims, 2 Drawing Sheets

PRIMER CONCENTRATIONS: EQUAL

| | LENGTH | [PRIMER] |
|---|---|---|
| A | 400 bp | 250 nM |
| B | 200 bp | 250 nM |
| C | 100 bp | 250 nM |

FIG. 2

MULTIPLEX PCR PRIMER CONCENTRATIONS AS A FUNCTION OF THE LENGTHS OF AMPLICONS

| VALUES OF X | 2 | 2 | 2 | 1 | 0 | 3 |
|---|---|---|---|---|---|---|
| TYPICAL VALUES OF $L_L$ | 1000 nM | 500 nM | 250 nM | 500 nM | 500 nM | 500 nM |

|  | AMPLICON | LENGTH | X=2, $L_L$=1000 | X=2, $L_L$=500 | X=2, $L_L$=250 | X=1, $L_L$=500 | X=0, $L_L$=500 | X=3, $L_L$=500 |
|---|---|---|---|---|---|---|---|---|
| LONGEST | 4 | 368 bp | 1000.0 nM | 500.0 nM | 250.0 nM | 500.0 nM | 500.0 nM | 500.0 nM |
|  | 5 | 272 bp | 546.3 nM | 273.2 nM | 136.6 nM | 369.6 nM | 500.0 nM | 201.9 nM |
|  | 8 | 241 bp | 428.9 nM | 214.4 nM | 107.2 nM | 327.4 nM | 500.0 nM | 140.4 nM |
|  | 11 | 231 bp | 394.0 nM | 197.0 nM | 98.5 nM | 313.9 nM | 500.0 nM | 123.7 nM |
|  | 10 | 210 bp | 325.6 nM | 162.8 nM | 81.4 nM | 285.3 nM | 500.0 nM | 92.9 nM |
|  | 6 | 204 bp | 307.3 nM | 153.7 nM | 76.8 nM | 277.2 nM | 500.0 nM | 85.2 nM |
|  | 7 | 175 bp | 226.1 nM | 113.1 nM | 56.5 nM | 237.8 nM | 500.0 nM | 53.8 nM |
|  | 2 | 164 bp | 198.6 nM | 99.3 nM | 49.7 nM | 222.8 nM | 500.0 nM | 44.3 nM |
|  | 9 | 146 bp | 157.4 nM | 78.7 nM | 39.4 nM | 198.4 nM | 500.0 nM | 31.2 nM |
| SHORTEST | 3 | 90 bp | 59.8 nM | 29.9 nM | 15.0 nM | 122.3 nM | 500.0 nM | 7.3 nM |

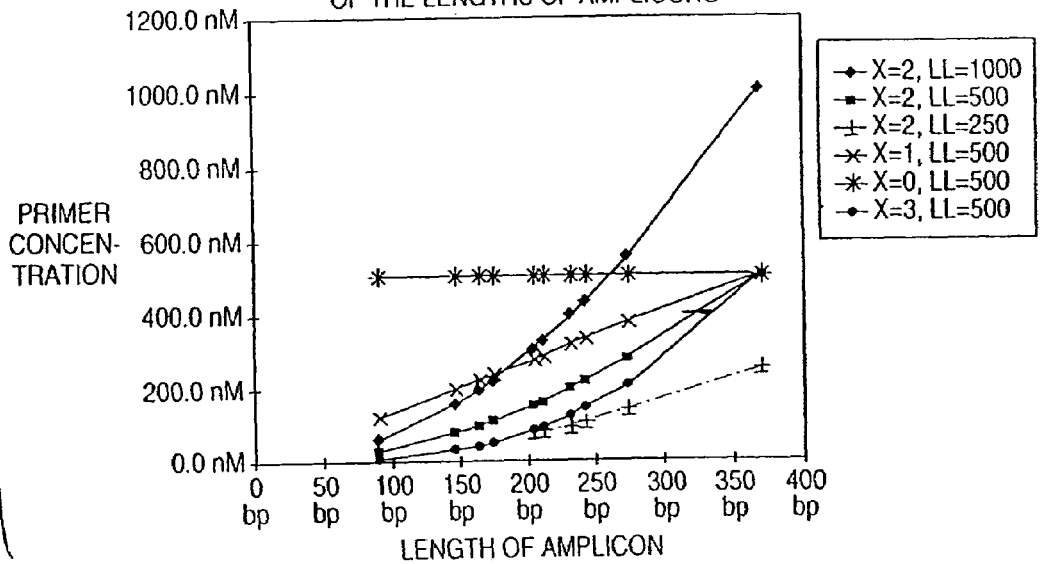

SEQUENCE LISTING

<160> NUMBER OF SEQ ID NOS: 20

<210> SEQ ID NO 1
<211> LENGTH: 28
<212> TYPE: DNA
<213> ORGANISM: homo sapiens

<400> SEQUENCE: 1
tcatgctgga tccccacttt tcctcttg                                    28

<210> SEQ ID NO 2
<211> LENGTH: 28

-continued

<210> SEQ ID NO 2
<211> LENGTH: 28
<212> TYPE: DNA
<213> ORGANISM: homo sapiens

<400> SEQUENCE: 2
tggcctgccc ttccaatgga tccactca                                    28

<210> SEQ ID NO 3
<211> LENGTH: 30
<212> TYPE: DNA
<213> ORGANISM: homo sapiens

<400> SEQUENCE: 3
aattcatggg actgactttc tgctcttgtc                                  30

<210> SEQ ID NO 4
<211> LENGTH: 26
<212> TYPE: DNA
<213> ORGANISM: homo sapiens

<400> SEQUENCE: 4
tccaggtccc agcccaaccc ttgtcc                                      26

<210> SEQ ID NO 5
<211> LENGTH: 30
<212> TYPE: DNA
<213> ORGANISM: homo sapiens

<400> SEQUENCE: 5
gtcctctgac tgctcttttc acccatctac                                  30

<210> SEQ ID NO 6
<211> LENGTH: 26
<212> TYPE: DNA
<213> ORGANISM: homo sapiens

<400> SEQUENCE: 6
gggatacggc caggcattga agtctc                                      26

<210> SEQ ID NO 7
<211> LENGTH: 28
<212> TYPE: DNA
<213> ORGANISM: homo sapiens

<400> SEQUENCE: 7
cttgtgccct gactttcaac tctgtctc                                    28

<210> SEQ ID NO 8
<211> LENGTH: 27
<212> TYPE: DNA
<213> ORGANISM: homo sapiens

<400> SEQUENCE: 8
tgggcaacca gccctgtcgt ctctcca                                     27

<210> SEQ ID NO 9
<211> LENGTH: 29
<212> TYPE: DNA
<213> ORGANISM: homo sapiens

<400> SEQUENCE: 9
ccaggcctct gattcctcac tgattgctc                                   29

```
<210> SEQ ID NO 10
<211> LENGTH: 27
<212> TYPE: DNA
<213> ORGANISM: homo sapiens

<400> SEQUENCE: 10
gccactgaca accaccctta acccctc                                27

<210> SEQ ID NO 11
<211> LENGTH: 27
<212> TYPE: DNA
<213> ORGANISM: homo sapiens

<400> SEQUENCE: 11
gcctcatctt gggcctgtgt tatctcc                                27

<210> SEQ ID NO 12
<211> LENGTH: 28
<212> TYPE: DNA
<213> ORGANISM: homo sapiens

<400> SEQUENCE: 12
ggccagtgtg cagggtggca agtggctc                               28

<210> SEQ ID NO 13
<211> LENGTH: 30
<212> TYPE: DNA
<213> ORGANISM: homo sapiens

<400> SEQUENCE: 13
gtaggacctg atttccttac tgcctcttgc                             30

<210> SEQ ID NO 14
<211> LENGTH: 29
<212> TYPE: DNA
<213> ORGANISM: homo sapiens

<400> SEQUENCE: 14
ataactgcac ccttggtctc ctccaccgc                              29

<210> SEQ ID NO 15
<211> LENGTH: 30
<212> TYPE: DNA
<213> ORGANISM: homo sapiens

<400> SEQUENCE: 15 cactttatc acctttcctt gcctctttcc                              30

<210> SEQ ID NO 16
<211> LENGTH: 30
<212> TYPE: DNA
<213> ORGANISM: homo sapiens

<400> SEQUENCE: 16
aactttccac ttgataagag gtcccaagac                             30

<210> SEQ ID NO 17
<211> LENGTH: 29
<212> TYPE: DNA
<213> ORGANISM: homo sapiens

<400> SEQUENCE: 17
acttacttct cccctcctc tgttgctgc                               29
```

```
<210> SEQ ID NO 18
<211> LENGTH: 31
<212> TYPE: DNA
<213> ORGANISM: homo sapiens

<400> SEQUENCE: 18
atggaatcct atggctttcc aacctaggaa g                              31

<210> SEQ ID NO 19
<211> LENGTH: 29
<212> TYPE: DNA
<213> ORGANISM: homo sapiens

<400> SEQUENCE: 19
catctctcct ccctgcttct gtctcctac                                 29

<210> SEQ ID NO 20
<211> LENGTH: 30
<212> TYPE: DNA
<213> ORGANISM: homo sapiens

<400> SEQUENCE: 20
ctgacgcaca cctattgcaa gcaagggttc                                30
```

METHODS AND COMPOSITIONS FOR MULTIPLEX AMPLIFICATION OF NUCLEIC ACIDS

RELATED APPLICATION

This is a divisional application of parent application Ser. No. 09/989,441, filed Nov. 21, 2001, now U.S. Pat. No. 6,673,579, which is a continuation application of application Ser. No. 09/099,301, filed Jun. 18, 1998, now U.S. Pat. No. 6,333,179, which is a non-provisional of application Ser. No. 60/050,405 filed on Jun. 20, 1997, the text of which are expressly incorporated by reference in their entirety herein.

BACKGROUND OF THE INVENTION

The polymerase chain reaction (PCR) is a simple and versatile method to amplify in vitro a specific segment of DNA for subsequent study (Saiki et al., Science 230:1350 (1985); Saiki et al., Science 235:487 (1985)). The PCR method has gained widespread use in biomedical research, and has revolutionized the accurate and early diagnosis of many inherited and acquired genetic disorders (Eisenstein, N. Engl. J. Med. 322:178 (1990)), particularly those caused by point mutations or small insertions or deletions including sickle cell anemia (Saiki et al., Science 230:1350 (1985)), hemophilia A (Kogan et al., N. Engl. J. Med. 317:985 (1987)), Tay-Sach's disease (Myerowitz, Proc. Natl. Acad. Sci. USA 85:3955 (1988); Myerowitz et al., J. Biol. Chem. 263:18587 (1988)), cystic fibrosis (Riordan et al., Science 245:1066 (1989)), and many others. With PCR, it is also possible to detect heterozygotic carriers in recessive disorders.

Polymerase chain reaction (PCR) is used for a variety of purposes. PCR can be used to amplify genomic DNA or other sources of nucleic acids for analysis. It is often desirable to be able to achieve equimolar yields of different length amplicons when performing multiplex PCR or multiple PCR reactions. Having an approximately equimolar yield of amplicons is particularly useful, for example, when approximately equal representation of certain regions of genomic DNA amplified after multiplex PCR is desired. Prior to the methods of present invention, finding the appropriate experimental conditions useful to achieve this result has been difficult because PCR amplifies nucleic acids having different lengths with different efficiencies. The yield of longer amplicons is often less than the yield of shorter amplicons because of those differences in PCR amplification efficiency. FIG. 1 shows the difference in yields that one might expect, for example, when starting with equal primer concentrations used to amplify amplicons of varying lengths: A, B, C. There is a continuing need in the art for methods which permit the amplification of different sequences with the same efficiency so that approximately equimolar products result.

SUMMARY OF THE INVENTION

It is an object of the present invention to provide a method of performing multiplex PCR which achieve approximately equimolar products.

It is another object of the invention to provide a set of primers for amplification of p53.

It is yet another object of the invention to provide a set of primers for amplification of p53 to achieve approximately equimolar products.

It is still another object of the invention to provide a mixture of primers for performing multiplex PCR.

These and other objects of the invention are provided by one or more of the embodiments provided below. In one embodiment of the invention a method of performing multiple polymerase chain reactions in a single vessel is provided. The method comprises the steps of priming DNA synthesis on a template in a vessel with at least two sets of primers. The primers are present in the vessel at a predetermined ratio which is described by the formula:

$$C_A = C_L(L_A \div L_L)^2$$

$C_A$ is the concentration of primers for an amplicon A. $C_L$ is the concentration of primer for the longest amplicon. $L_A$ is the length of the amplicon A. $L_L$ is the length of the longest amplicon.

Another embodiment provided by the invention is a method of performing multiple polymerase chain reactions in a single vessel. The method comprises priming DNA synthesis on a genomic p53 template in a vessel with ten sets of primers which amplify exons 2–11 of p53. The primers are shown in SEQ ID NO: ID NOS: 1–20. The primers are present in the vessel at the following ratio: exon 2 (89.4): exon 3 (26.9): exon 4 (450): exon 5 (245.8): exon 6 (138.3): exon 7 (101.8): exon 8 (193.0): exon 9 (70.8): exon 10 (146.5): exon 11 (177.3).

According to still another embodiment of the invention a set of primers for performing multiple polymerase chain reactions in a single vessel is provided. The set comprises twenty primers having sequences as shown in SEQ ID NO: 1–20.

According to yet another embodiment of the invention a mixture of primers for performing multiplex polymerase chain reaction is provided. The primers are present in the mixture at a predetermined ratio to each other. The ratio of the concentrations of the primers is described by:

$$C_A = C_L(L_A \div L_L)^2$$

wherein $C_A$ is the concentration of primers for an amplicon A; wherein $C_L$ is the concentration of primer for the longest amplicon; wherein $L_A$ is the length of the amplicon A; and wherein $L_L$ is the length of the longest amplicon.

The present invention thus provides the art with a method useful for performing multiplex PCR. This method is particularly useful for amplification of multiple exons of p53. Moreover, a particular primer set useful for performing such multiplex PCR is also provided.

BRIEF DESCRIPTION OF THE DRAWINGS

FIG. 2 illustrates the relationship for given values X and $L_L$, using the amplicons from different exons of the human p53 gene as an example.

DETAILED DESCRIPTION OF THE INVENTION

Figure 1:
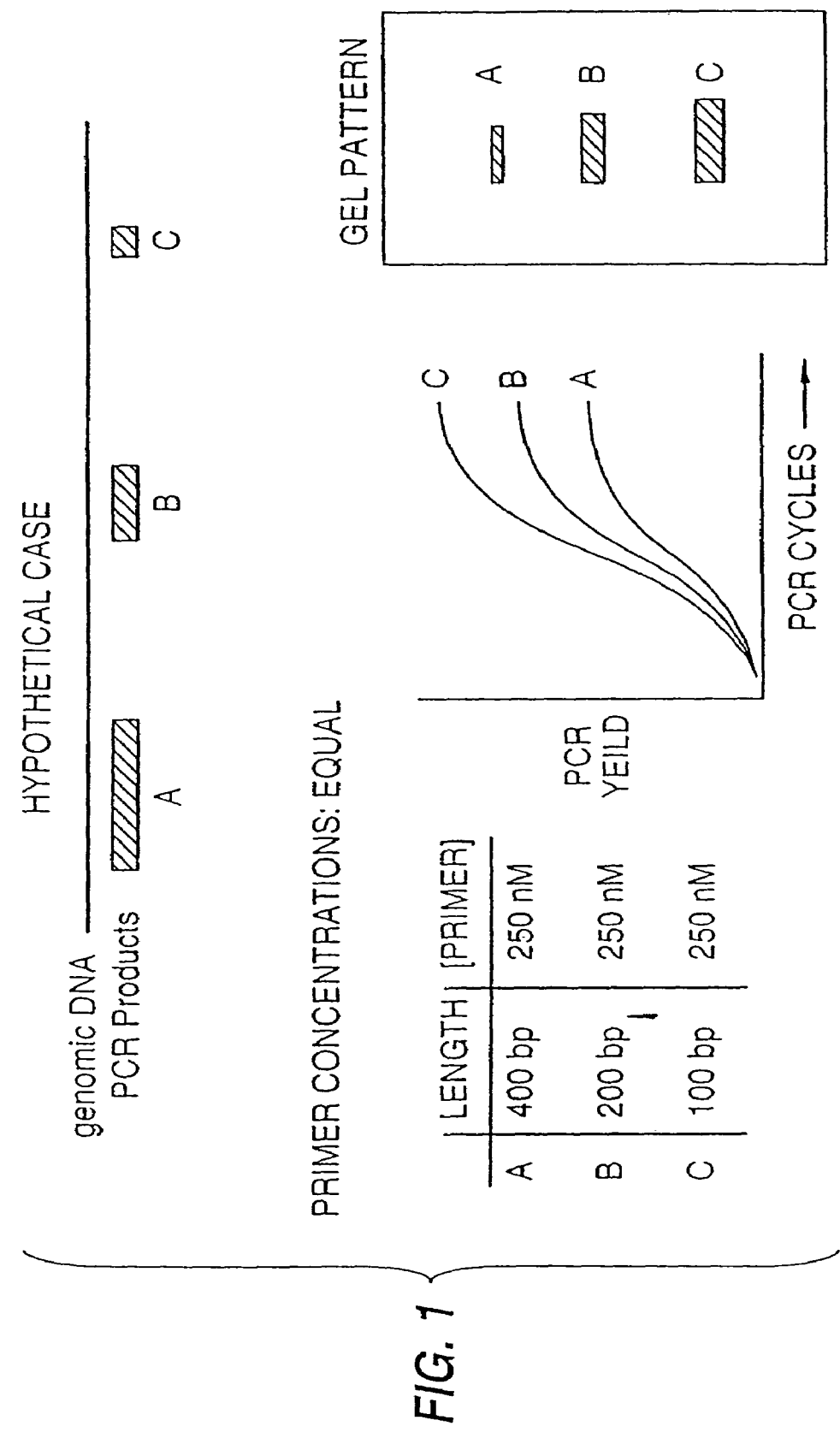
FIG. 1 shows the difference in yields that one might expect, for example, when starting with equal primer concentrations used to amplify amplicons of varying lengths: A, B, C.

It is a discovery of the present invention that approximately equimolar yields of amplicons of varying lengths can be easily produced by multiplex PCR. It has been determined that varying the primer concentrations as a function of the lengths of amplicons yields approximately equimolar amounts of amplicons of varying lengths. The relationship between primer concentration and the length of amplicons is as follows:

$$C_A = C_L(L_A/L_L)^X$$

wherein $C_A$=the concentration of primers for an amplicon A;

$C_L$=the concentration of primer for the longest amplicon;
$L_A$=the length of amplicon A;
$L_L$=the length of the longest amplicon; and
X is usually not zero and is often between one and three.

This relationship can be placed in a computer readable medium or be used with a computer system if desired.

FIG. 2 illustrates the relationship for given values X and $L_L$, using the amplicons from different exons of the human p53 gene as an example. Using primer concentrations as set forth, for example in FIG. 2, one skilled in the art can determine the optimum set of primer concentrations to yield approximately equimolar yields of varying length amplicons in a multiplex or multiple PCR. Preferably, primers having both comparable base composition and comparable melting temperatures are used. Also preferably, $Mg^{+2}$ concentration, annealing temperatures, and cycling times of the PCR are optimized prior to choosing the desired set of primer concentrations in accordance with the present invention.

PCR techniques applicable to the present invention include inter alia those discussed in PCR PRIMER: A LABORATORY MANUAL, Dieffenbach, C. W. and Dveksler, G. S., eds., Cold Spring Harbor Laboratory Press (1995).

The present application further provides primer sequences, primer concentrations, and experimental conditions useful in the amplification of the coding region of the human p53 gene. Particularly useful primers for amplification of exons of the p53 gene are set forth in Table 1.

Table 2 shows particularly useful concentrations of the primers set forth in Table 1 for multiplex PCR amplification using the experimental conditions set forth in Table 3.

TABLE 2

Primer Concentrations in p53 Primer Set

Values of X: 2

Typical values of $C_L$: 450 nM

|  | Amplicon | Length | Primer Concs |
|---|---|---|---|
| Longest | 4 | 368 bp | 450.0 nM |
|  | 5 | 272 bp | 245.8 nM |
|  | 8 | 241 bp | 193.0 nM |
|  | 11 | 231 bp | 177.3 nM |
|  | 10 | 210 bp | 146.5 nM |
|  | 6 | 204 bp | 138.3 nM |
|  | 7 | 175 bp | 101.8 nM |
|  | 2 | 164 bp | 89.4 nM |
|  | 9 | 146 bp | 70.8 nM |
| Shortest | 3 | 90 bp | 26.9 nM |

TABLE 3

Multiplex PCR
Start with 250 ng of Template DNA.
PCR Components for 100 ul PCR in 0.2 ml thin walled tubes:

|  | Stock Conc | Final Conc | for 1 reaction |
|---|---|---|---|
| Buffer (No Mg) | 10 X | 1 X | 10.0 ul |
| $MgCl_2$ | 25 mM | 2.5 mM | 10.0 ul |
| dATP | 10 mM | 200 uM | 2.0 ul |

TABLE 1 p53 Primer Set
20 primers in 1 mM Tris-HCl, pH 7.4, 0.1 mM
EDTA, sequences:

| Exon 2: | 5'-TCATGCTGGATCCCCACTTTTCCTCTTG-3' | (SEQ ID NO: 1) |
|---|---|---|
|  | 5'TGGCCTGCCCTTCCAATGGATCCACTCA-3' | (SEQ ID NO: 2) |
| Exon 3: | 5'-AATTCATGGGACTGACTTTCTGCTCTTGTC-3' | (SEQ ID NO: 3) |
|  | 5'-TCCAGGTCCCAGCCCAACCCTTGTCC-3' | (SEQ ID NO: 4) |
| Exon 4: | 5'-GTCCTCTGACTGCTCTTTTCACCCATCTAC-3' | (SEQ ID NO: 5) |
|  | 5'-GGGATACGCCCAGGCATTGAAGTCTC-3' | (SEQ ID NO: 6) |
| Exon 5: | 5'-CTTGTGCCCTGACTTTCAACTCTGTCTC-3' | (SEQ ID NO: 7) |
|  | 5'-TGGGCAACCAGCCCTGTCGTCTCTCCA-3 | (SEQ ID NO: 8) |
| Exon 6: | 5'-CCAGGCCTCTGATTCCTCACTGATTGCTC-3' | (SEQ ID NO: 9) |
|  | 5'-GCCACTGACAACCACCCTTAACCCCTC-3' | (SEQ ID NO: 10) |
| Exon 7: | 5'-GCCTCATCTTGGGCCTGTGTTATCTCC-3' | (SEQ ID NO: 11) |
|  | 5'-GGCCAGTGTGCAGGGTGGCAAGTGGCTC-3' | (SEQ ID NO: 12) |
| Exon 8: | 5'-GTAGGACCTGATTTCCTTACTGCCTCTTGC-3' | (SEQ ID NO: 13) |
|  | 5'-ATAACTGCACCCTTGGTCTCCTCCACCGC-3' | (SEQ ID NO: 14) |
| Exon 9: | 5'-CACTTTTATCACCTTTCCTTGCCTCTTTCC-3' | (SEQ ID NO: 15) |
|  | 5'-AACTTTCCACTTGATAAGAGGTCCCAAGAC-3' | (SEQ ID NO: 16) |
| Exon 10: | 5'-ACTTACTTCTCCCCCTCCTCTGTTGCTGC-3' | (SEQ ID NO: 17) |
|  | 5'-ATGGAATCCTATGGCTTTCCAACCTAGGAAG-3' | (SEQ ID NO: 18) |
| Exon 11: | 5'-CATCTCTCCTCCCTGCTTCTGTCTCCTAC-3' | (SEQ ID NO: 19) |
|  | 5'-CTGACGCACACCTATTGCAAGCAAGGGTTC-3' | (SEQ ID NO: 20) |

TABLE 3-continued

Multiplex PCR
Start with 250 ng of Template DNA.
PCR Components for 100 ul PCR in 0.2 ml thin walled tubes:

| | | | |
|---|---|---|---|
| dCTP | 10 mM | 200 uM | 2.0 ul |
| dGTP | 10 mM | 200 uM | 2.0 ul |
| dTTP | 10 mM | 200 uM | 2.0 ul |
| Taq GOLD | 5 U/ul | 10 U | 2.0 ul |
| p53 Primer Set | 20 X | 1 X | 5.0 ul |
| Water | | | |
| Human genomic DNA | | 250 ng | |
| | | Total Volume | 100.0 ul |

Final Concentrations in Buffer (No Mg) are 10 mM Tris-HCl (pH 8.3), 50 mM KCl Taq GOLD is AmpliTaq Gold ™ from Perkin Elmer catalog # N808-0243

PCR Cycles:

| | | |
|---|---|---|
| 35 Cycles: | 94 C. | 10 min |
| | 94 C. | 30 sec |
| | 60 C. | 30 sec |
| | 72 C. | 45 sec |
| | 72 C. | 10 min |

To visualize amplicons by gel Analysis:
Visualize PCR Products on 4% NuSieve Agarose Gel
NuSieve ™ Agarose 3:1 is from FMC catalog # 50092
Load 5 ul of PCR + loading buffer
Use 50 bp Ladder (Gibco/BRL catalog # 10416-014) as size marker
Run gel at 125 Volts for 30 min. to 90 min.

| Amplicon | Length |
|---|---|
| Expected PCR Products: | |
| Exon 2 | 164 bp |
| Exon 3 | 90 bp |
| Exon 4 | 368 bp |
| Exon 5 | 272 bp |
| Exon 6 | 204 bp |
| Exon 7 | 175 bp |
| Exon 8 | 241 bp |
| Exon 9 | 146 bp |
| Exon 10 | 210 bp |
| Exon 11 | 225 bp |
| Order in Gel: | |
| Exon 4 | 368 bp |
| Exon 5 | 272 bp |
| Exon 8 | 241 bp |
| Exon 11 | 225 bp |
| Exon 10 | 210 bp |
| Exon 6 | 204 bp |
| Exon 7 | 175 bp |
| Exon 2 | 164 bp |
| Exon 9 | 146 bp |
| Exon 3 | 90 bp |

Using the methods and reagents provided herein, we achieved multiplex PCR amplification of coding regions shown of the human p53 gene in approximately equimolar amounts. That desirable result was achieved in a single-tube reaction. The achievement of such desirable results with the remarkable convenience of a single tube reaction further illustrates the contribution to the art made by the present invention.

The methods and compositions of the present invention are useful in virtually any context in which equimolar yields of various PCR products are desired. Such contexts include without limitation paternity testing, forensic analysis, genetic screening, polymorphism detection, and mutation analyses. The present invention can be used to amplify nucleic acids for all forms of sequence analysis known to those skilled in the art. Sequence analysis techniques includes, for example, dideoxy-sequencing and sequence analysis using high-density nucleic acid arrays: the Gene-Chip® probe arrays or VLSIPS™ technology of Affymetrix Inc. High density nucleic acid arrays are discussed for example in Chee, M., Yang, R, Hubbell, E., Berno, A., Huang, X. C., Stern, D., Winkler, J., Lockhart, D. J., Morris, M. S., & Fodor, S. P., Science 5287, 610–614 (1996), U.S. Pat. No. 5,445,934, and International Publication No. WO 95/11995 corresponding to PCT Application No. PCT/US94/12305.

The p53 gene and its protein product are discussed in *Molecular Biology of the Cell,* 3rd Edition, Alberts, B., Bray, D., Lewis, J., Raff, M., Roberts, K., and Watson, J. D., Garland Publishing (1994) at pages 889 and 1284–1289.

It is understood that the examples and embodiments described herein are for illustrative purposes only and that various modifications or changes in light thereof will be suggested to persons skilled in the art and are to be included within the spirit and purview of this application and scope of any appended claims. All publications, patents, and patent applications cited herein are hereby incorporated by reference in their entirety for all purposes.

The invention claimed is:

1. A mixture of primer pairs for performing multiplex polymerase chain reaction, wherein each of the primer pairs is present in the mixture at a predetermined ratio to each other, wherein the ratio of the molar concentrations of the primer pairs is described by:

$$C_A = C_L (L_A + L_L)^2$$

wherein $C_A$ is the concentration of primers for an amplicon A; wherein $C_L$ is the concentration of primers for the longest amplicon; wherein $L_A$ is the length in base pairs of the amplicon A; wherein $L_L$ is the length in base pairs of the longest amplicon: wherein $L_A$ is not equal to $L_L$.

2. The mixture of claim 1 which comprises at least 4 primers.

3. The mixture of claim 1 which comprises at least 6 primers.

4. The mixture of claim 1 which comprises at least 8 primers.

5. The mixture of claim 1 which comprises at least 10 primers.

6. The mixture of claim 1 which comprises at least 12 primers.

7. The mixture of claim 1 which comprises at least 14 primers.

8. The mixture of claim 1 which comprises at least 16 primers.

9. The mixture of claim 1 which comprises at least 18 primers.

10. The mixture of claim 1 which comprises at least 20 primers.

11. A mixture of primers for performing multiplex polymerase chain reaction, comprising at least six primers which are present in the mixture at a predetermined ratio to each other, wherein the ratio of the molar concentrations of the primers is described by:

$$C_A = C_L (L_A L_L)^2$$

wherein $C_A$ is the concentration of primers for an amplicon A; wherein $C_L$ is the concentration of primers for the longest amplicon; wherein $L_A$ is the length in base pairs of the amplicon A; wherein $L_L$ is the length in base pairs of the longest amplicon: and wherein LA is not equal to $L_L$.

12. The mixture of claim 11 which comprises at least 8 primers.

13. The mixture of claim 11 which comprises at least 110 primers.

14. The mixture of claim 11 which comprises at least 12 primers.

15. The mixture of claim 11 which comprises at least 14 primers.

16. The mixture of claim 11 which comprises at least 16 primers.

17. The mixture of claim 11 which comprises at least 18 primers.

18. The mixture of claim 11 which comprises at least 20 primers.

* * * * *